United States Patent
Kodama et al.

(10) Patent No.: US 7,297,944 B2
(45) Date of Patent: Nov. 20, 2007

(54) ION BEAM DEVICE AND ION BEAM PROCESSING METHOD, AND HOLDER MEMBER

(75) Inventors: Toshio Kodama, Chiba (JP); Masakatsu Hasuda, Chiba (JP); Toshiaki Fuji, Chiba (JP); Kouji Iwasaki, Chiba (JP); Yasuhiko Sugiyama, Chiba (JP); Yasuyuki Takagi, Chiba (JP)

(73) Assignee: SII NanoTechnology Inc. (JP)

( * ) Notice: Subject to any disclaimer, the term of this patent is extended or adjusted under 35 U.S.C. 154(b) by 27 days.

(21) Appl. No.: 10/520,982

(22) PCT Filed: Jul. 9, 2003

(86) PCT No.: PCT/JP03/08691

§ 371 (c)(1),
(2), (4) Date: Mar. 14, 2005

(87) PCT Pub. No.: WO2004/008475

PCT Pub. Date: Jan. 22, 2004

(65) Prior Publication Data

US 2005/0236587 A1  Oct. 27, 2005

(30) Foreign Application Priority Data

Jul. 12, 2002  (JP) .............................. 2002-204028

(51) Int. Cl.
*H01J 37/30* (2006.01)
*H01J 37/317* (2006.01)
*G01N 1/28* (2006.01)
*H01J 37/20* (2006.01)

(52) U.S. Cl. ...................... 250/304; 250/311; 250/307; 250/442.11

(58) Field of Classification Search ................ 250/311, 250/307, 310, 442.11, 304
See application file for complete search history.

(56) References Cited

U.S. PATENT DOCUMENTS

| 5,574,280 | A | * | 11/1996 | Fujii et al. ................... 250/309 |
| 5,986,264 | A | * | 11/1999 | Grunewald .................. 250/310 |
| 6,838,685 | B1 | * | 1/2005 | Kodama et al. ........ 250/442.11 |
| 7,002,152 | B2 | * | 2/2006 | Grunewald ................. 250/311 |
| 2002/0005492 | A1 | * | 1/2002 | Hashikawa et al. ..... 250/442.11 |

FOREIGN PATENT DOCUMENTS

| JP | 03254055 | 11/1991 |
| JP | 04116843 | 4/1992 |
| JP | 04120437 | 4/1992 |
| JP | 08106873 | 4/1996 |
| JP | 10221227 | 8/1998 |
| JP | 2000258314 | 9/2000 |

* cited by examiner

Primary Examiner—Jack I. Berman
(74) Attorney, Agent, or Firm—Adams & Wilks

(57) ABSTRACT

An apparatus has a holder member (21) which holds a sample (3), and a removing beam source (13) which irradiates an inert ion beam onto a cross section (4) of the sample (3) held by a holder member (21) and removes a fracture layer on the cross section (4). Then, the removing beam source (13) is disposed on the holding end side of the sample (3) with respect to the normal L of the cross section (4) so that the irradiating direction of the inert ion beam is tilted at the tilt angle θ to the normal L with respect to the cross section (4).

15 Claims, 10 Drawing Sheets

FIG. 3
(a)
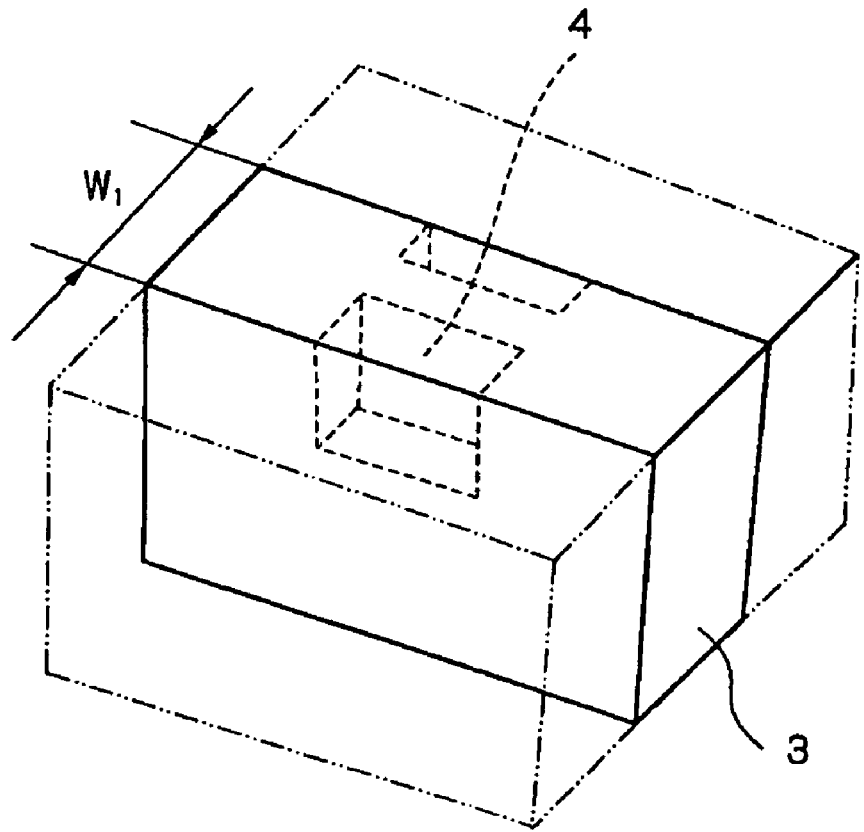
(b)
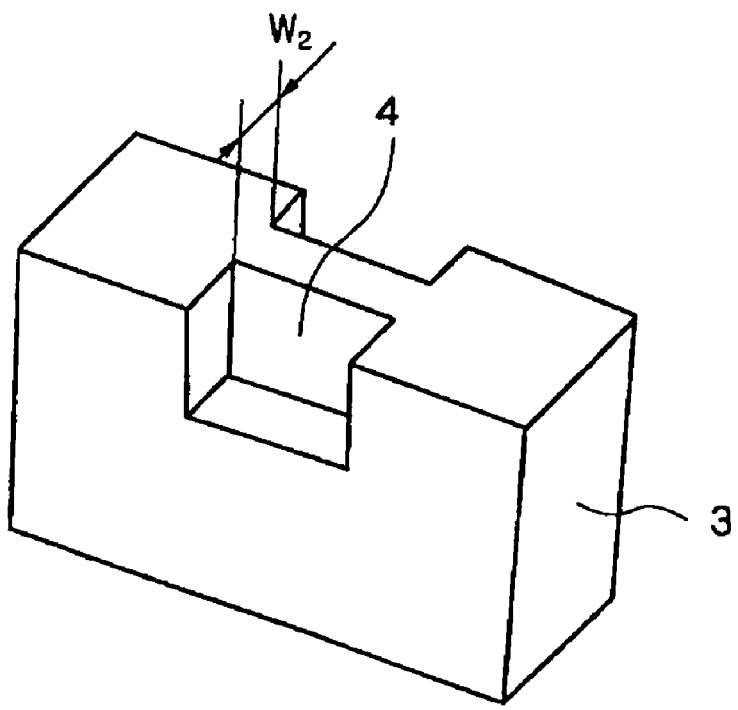

ION BEAM DEVICE AND ION BEAM PROCESSING METHOD, AND HOLDER MEMBER

CROSS REFERENCE TO RELATED APPLICATIONS

This application is a U.S. national stage application of copending International Application No. PCT/JP03/08691, filed Jul. 9, 2003, claiming a priority date of Jul. 12, 2002, and published in a non-English language.

TECHNICAL FIELD

The present invention relates to an ion beam apparatus, an ion beam processing method and a holder member for processing a cross section for observation in a sample that is used to observe a micro-structure of a semiconductor and the like, for example.

BACKGROUND ART

Traditionally, for example, an ion beam apparatus is widely used for the purpose of preparing a TEM sample that is used to observe defects generated in wafer fabrication processes of semiconductor memory and the like by a TEM (Transmission Electron Microscope) and the like. In this type of ion beam apparatus, ion beam fabrication by the focused ion beam (FIB: Focused Ion Beam) allows processing a micro-cross section for observation in a particular portion of a TEM sample, and allows preparing the TEM sample for a relatively short time.

However, when the traditional ion beam apparatus is used to perform ion beam fabrication for forming a micro-cross section in a sample, gallium used for an ion source of the focused ion beam is injected into the cross section of the sample to alter the sample amorphously, and gallium forms a damage layer which is a so-called fracture layer with the damaged cross section. Since the sample having this fracture layer formed on the observation cross section adversely affects relatively high-powered TEM observation by the fracture layer, there is a disadvantage that a normal crystal lattice image cannot be obtained, causing a problem in highly accurate observation up to the atomic level of the cross section. Therefore, the fracture layer needs to be removed so that the fracture layer of about 30 nm formed on the cross section of the sample is reduced up to about 10 nm.

Then, it is considered that the acceleration energy of the focused ion beam is reduced to decrease the thickness of the fracture layer, or that after fabrication by the focused ion beam, an ion beam of relatively low energy is irradiated onto the cross section to remove the fracture layer formed on the cross section. Furthermore, the ion beam for removing the fracture layer is irradiated onto the cross section to form a new fracture layer on the cross section as well. However, a fracture layer formed by using an argon ion beam, for example, is about a few nm, and thus it does not cause problems in observing the cross section.

Accordingly, for the traditional ion beam apparatus, an apparatus is proposed which has a removing beam part that irradiates an argon ion beam onto the cross section of a sample formed by irradiating a focused ion beam and removes a fracture layer on the cross section.

This traditional ion beam apparatus has a holder part which holds a sample, a processing beam part which processes a cross section in the sample, the removing beam part which removes the fracture layer on the cross section processed in the sample, and an observing beam part which observes the cross section of the sample. The holder part has a holder member which holds the sample on the tip end side thereof. The processing beam part is disposed vertically above as facing the top surface side of the sample held by the holder member. The removing beam part and the observing beam part are disposed at the positions to sandwich and face the cross section of the sample.

In the traditional ion beam apparatus thus configured, the processing beam part irradiates the focused ion beam from a gallium ion source onto the sample held by the holder member to process the cross section, and the removing beam part irradiates the argon ion beam onto the cross section of the sample to remove the fracture layer of the cross section (ion milling). Then, the observing beam part irradiates an electron beam onto the cross section of the sample where the fracture layer has been removed, and an observed image of the cross section of the sample is obtained.

In the traditional ion beam apparatus described above, as shown in FIG. 11, in irradiating an argon ion beam onto a cross section 104 of a sample 103, the argon ion beam is widely irradiated onto the area other than the cross section 104 of the sample 103. Therefore, the argon ion beam is irradiated onto a step part and the like adjacent to the base end side of the cross section 104 of the sample 103, and is partially irradiated onto the top surface and the like of the step part to fly or eject secondary particles of the fracture layer, causing a problem that the secondary particles of the removed fracture layer are again attached onto the cross section 104 and contaminate it.

Then, an object of the invention is to provide an ion beam apparatus, an ion beam processing method, and the holder member, which can excellently remove the fracture layer from the processed surface of the sample.

BACKGROUND OF THE INVENTION

In order to achieve the above object, an ion beam apparatus according to the invention has a holder member which holds a sample; and a removing beam source which irradiates a gaseous ion beam onto a processed surface of a sample held by the holder member and removes a fracture layer on the processed surface, the processed surface being formed by irradiating a focused ion beam. The gaseous ion beam is irradiated from a holding end side of the sample with respect to a direction vertical to the processed surface so that its irradiating direction is tilted with respect to the vertical direction.

According to the ion beam apparatus of the invention thus configured, when the gaseous ion beam is irradiated onto the sample and the fracture layer is removed, the gaseous ion beam is irradiated onto a step part formed adjacent to the processed surface, and thus secondary particles are ejected. However, the ejected secondary particles do not travel in the direction where they reach the processed surface. Therefore, it is reduced that the fracture layer removed by the gaseous ion beam is again attached onto the processed surface.

Furthermore, the holder member provided to the ion beam apparatus according to the invention preferably has a base part which is rotatably supported about a first axis in parallel with a horizontal direction, and a holding part which is rotatably disposed about a second axis orthogonal to the first axis at a tip end side of the base part and holds the sample. The holder member is rotatably disposed about the first axis, and thus the arrangement of the removing beam source with respect to the holder member and the flexibility in the irradiating direction of the gaseous ion beam can be secured.

Moreover, the holder member has the holding part which is rotatably disposed about the second axis, and thus the irradiating directions of the focused ion beam and the gaseous ion beam can be varied with respect to the sample held by the holding part.

Besides, an ion beam processing method according to the invention has a first step of irradiating a focused ion beam onto a sample and forming a processed surface; and a second step of irradiating a gaseous ion beam onto the processed surface of the sample and removing a fracture layer on the processed surface. And, at the second step, the gaseous ion beam is irradiated from a holding end side of the sample with respect to a direction vertical to the processed surface of the sample so that its irradiating direction is tilted with respect to the vertical direction.

In the ion beam processing method according to the invention thus configured, at the second step, the gaseous ion beam is irradiated from the holding end side of the sample with respect to the direction vertical to the processed surface of the sample so that its irradiating direction is tilted with respect to the vertical direction. Therefore, the gaseous ion beam is irradiated onto the step part formed adjacent to the processed surface, and thus secondary particles of the fracture layer are ejected. However, the ejected secondary particles travel in the direction where they do not reach the processed surface. Accordingly, it is reduced that the secondary particles of the fracture layer removed by the gaseous ion beam are again attached onto the processed surface.

In addition, the holder member according to the invention has: a base part which is rotatably supported about a first axis in parallel with the horizontal direction; and a holding part which is rotatably disposed about a second axis orthogonal to the first axis at a tip end side of the base part and holds a sample where a focused ion beam is irradiated to form a processed surface.

According to the holder member of the invention thus configured, when an ion beam is irradiated onto the sample to form the processed surface, the holding part is rotated about the second axis with respect to the irradiating direction of the ion beam. Thus, the irradiating direction of the ion beam can be varied with respect to the processed surface of the sample. Accordingly, the irradiating direction of the ion beam is varied with respect to the processed surface and processing by the ion beam is repeated for several times. Then, streaks generated in the processed surface are gradually reduced in the sample held by the holding part when fine bumps and dips and the border between different materials exist on the top surface of the sample, removing the streaks. Furthermore, the streaks described above are also removed from the sample even when processing by the ion beam is done as the irradiating direction of the ion beam is varied with respect to the processed surface.

Moreover, for the gas described above, for example, oxygen, argon, helium, neon, xenon, krypton, radon and the like are named as they do not greatly affect the characteristics of the sample.

Besides, the fracture layer in the invention is, for example, the layer that is altered amorphously by injecting gallium into the processed surface and damaged by gallium when the focused ion beam of gallium is irradiated onto the processed surface of the sample.

In addition, the holding end side of the sample described above is the end side of the sample held by the holder member which is contacted with the holder member. For example, it is the end side of the sample facing the holding surface of the holder member on which a support is contacted when a small piece of the sample is held by the holder member through the support such as a dice.

BRIEF DESCRIPTION OF THE DRAWINGS

FIG. 3(a) is a perspective diagram illustrating a sample in which a cross section is processed, and FIG. 3(b) is a perspective diagram illustrating the sample in which the cross section has been processed;

DETAILED DESCRIPTION OF THE INVENTION

Hereinafter, specific embodiments according to the invention will be described with reference to the drawings.

Figure 1:
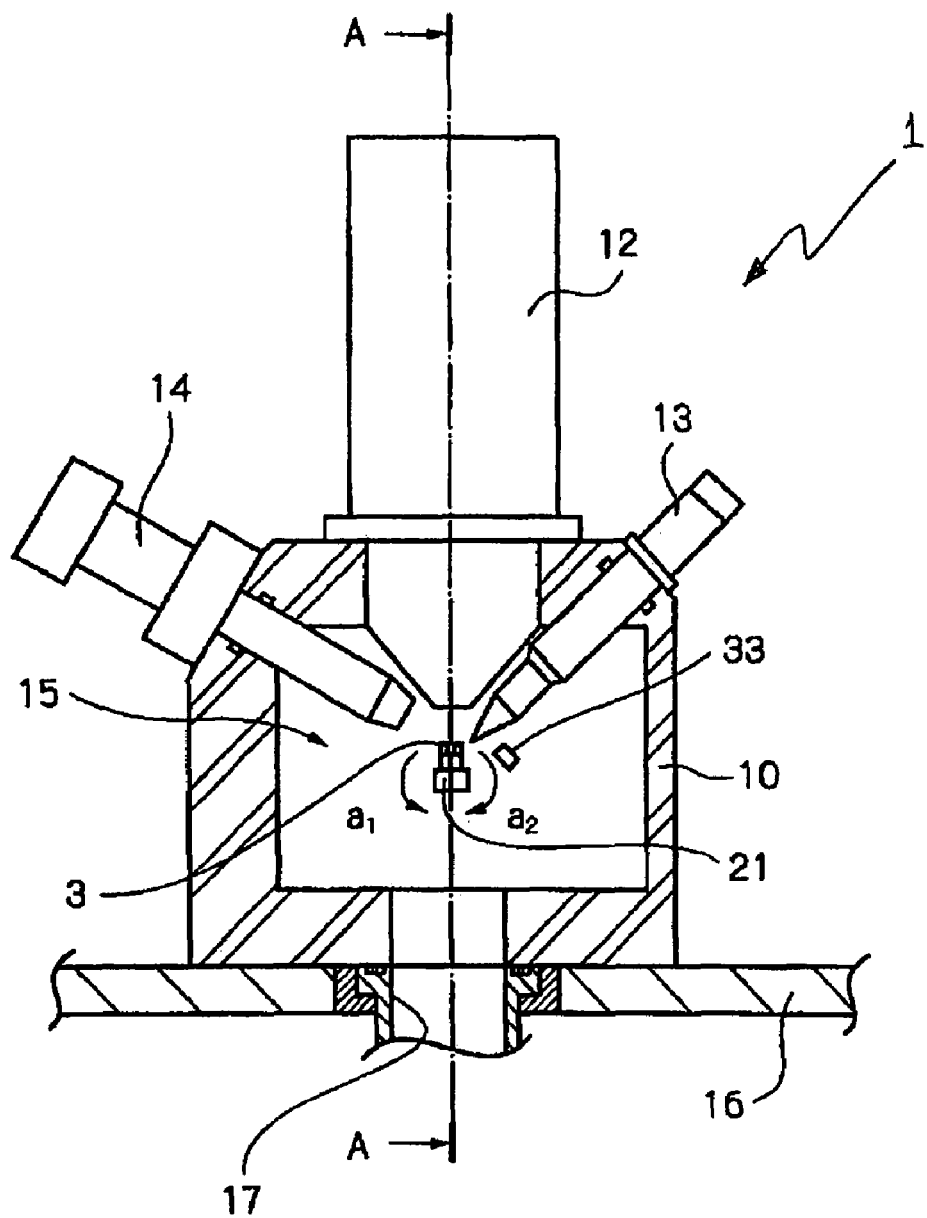
FIG. 1 is a cross section schematically illustrating an ion beam apparatus according to the invention.
Figure 2:
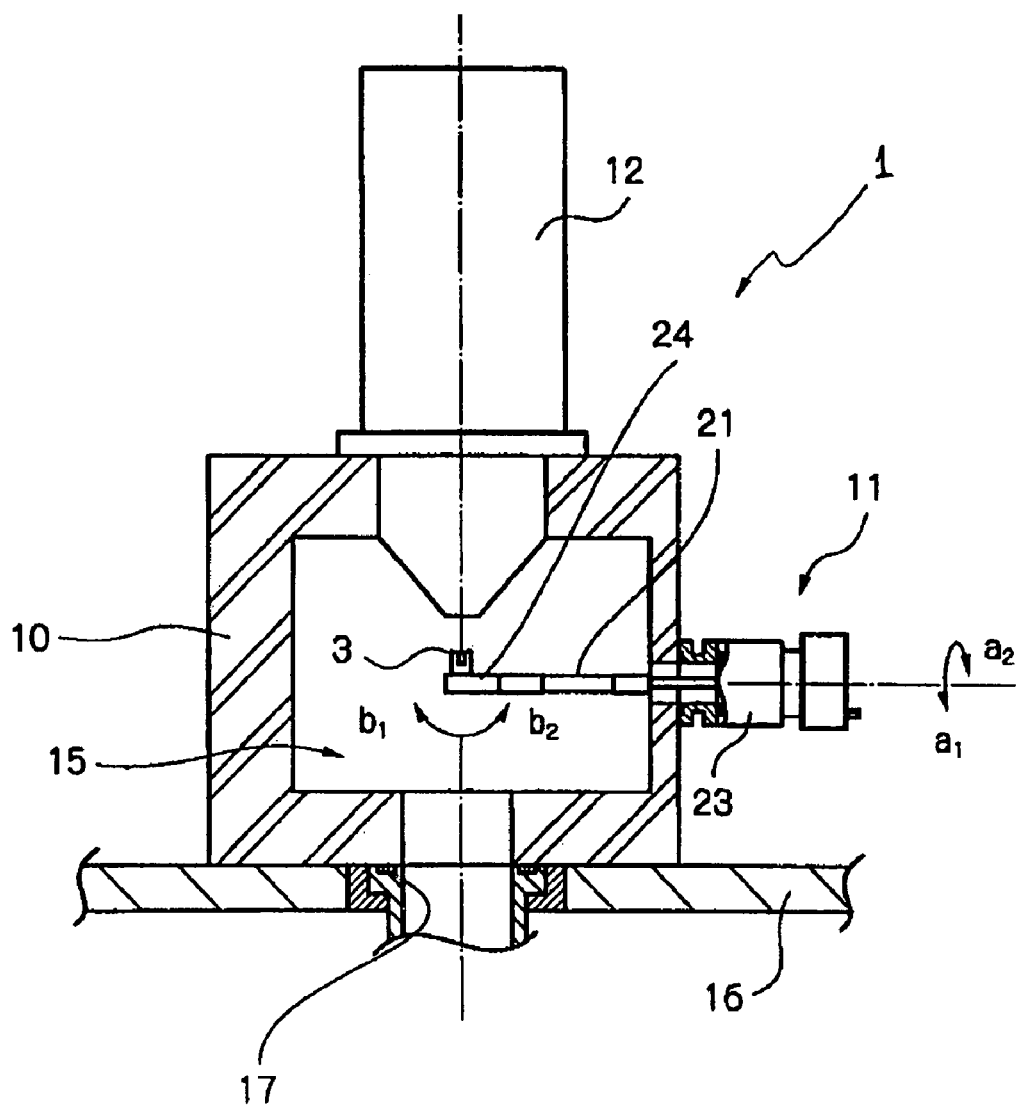
FIG. 2 is a cross-section of A-A schematically illustrating the ion beam apparatus shown in FIG. 1.

As shown in FIGS. 1 and 2, an ion beam apparatus 1 of this embodiment is a so-called side entry ion beam apparatus, having a vacuum container 10 which processes a sample 3 therein, a holder part 11 which holds the sample 3, a processing beam part 12 in the form of a focused ion beam unit which irradiates a focused ion beam from a gallium ion source onto the sample 3 and processes an observation cross section, a removing beam unit or part 13 which irradiates an inert ion beam onto the cross section processed in the sample 3 and removes a fracture layer on the cross section, and an observing beam unit or part 14 which irradiates an electron beam onto the cross section of the sample 3 and to enable observation of the cross section.

First, the sample 3 to be processed by the ion beam apparatus 1 is cut out of a wafer in a given flat plate, and then the both ends thereof cut in the width direction to form it in a block shape as shown in FIG. 3(a) beforehand. Then, the sample 3 in a block shape is formed to have the width $W_1$ of about 0.1 to 0.5 mm. As shown in FIG. 3(b), an observation cross section 4 is processed on the both ends thereof in the width direction by the ion beam apparatus 1 of the embodiment, and the width $W_2$ on the tip end side is formed in about a few tens μm, for example.

Furthermore, in the sample 3, a processed surface is formed only on one side in the width direction when the reflection mode for detecting secondary electrons reflected in the cross section 4 is used. Moreover, for the sample 3 in which the cross section 4 is observed by the ion beam apparatus 1 of the embodiment, it is acceptable to apply a sample that a small piece with a processed cross section is cut out by pickup or by liftout and is joined on a dice, other than the sample that is cut out in a block shape by dicing to form the cross section as described above.

The vacuum container 10 has a vacuum chamber 15 which processes and observes the sample 3, the container is disposed and fixed on a mounting base 16. The vacuum chamber 15 is communicated with an exhaust apparatus (not shown in the drawing) through an exhaust pipe 17.

The holder part 11 is disposed on the side surface part of the vacuum container 10, having a holder member 21 in a rod shape which rotatably holds the sample 3 in the directions of arrows $a_1$, $a_2$ in FIG. 1 and the directions of $b_1$, $b_2$.

Figure 4:
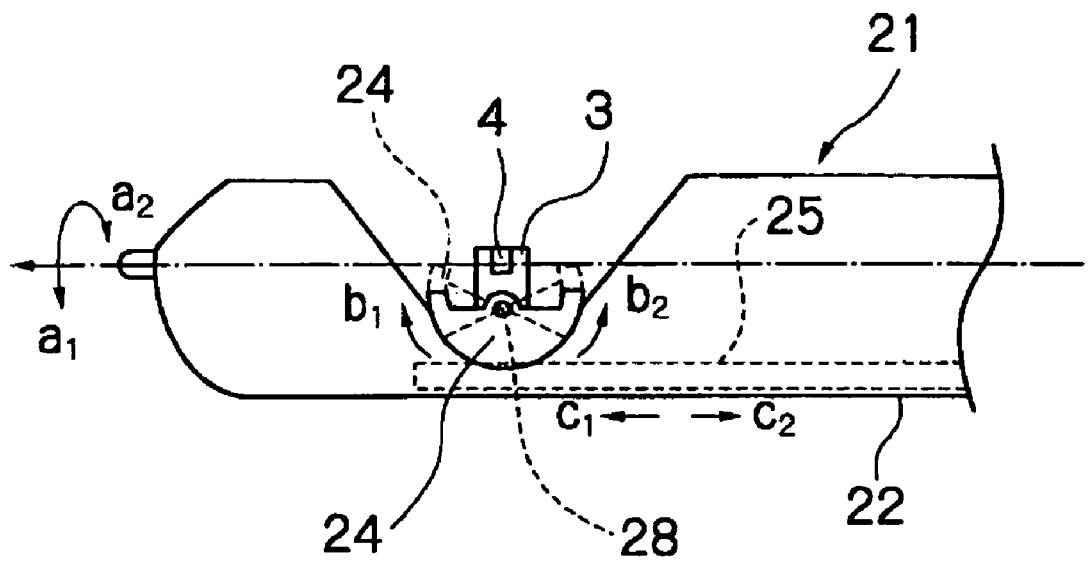
FIG. 4 is a perspective side view schematically illustrating a holding part of a holder member.
Figure 5:
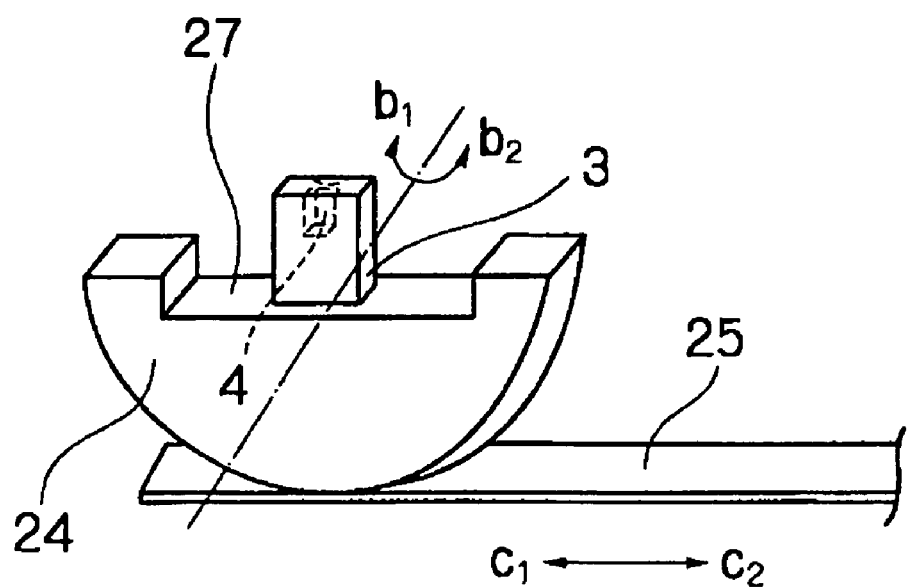
FIG. 5 is a schematic diagram illustrating the holding part and a slide plate.

As shown in FIGS. 4 and 5, the holder member 21 has a base part 22 which its longitudinal side is disposed in parallel with the horizontal direction, a holder support mechanism 23 which rotatably supports the base end side of the base part 22 in the directions of $a_1$, $a_2$, a holding part 24 which is rotatably disposed on the tip end side of the base part 22 in the directions of $b_1$, $b_2$ and holds the sample, and a slide plate 25 which rotates the holding part 24 with respect to the base part 22.

The base part 22 is supported by the holder support mechanism 23 rotatably at an angle of about 145 degrees in the direction of $a_1$ and at an angle of about 35 degrees in the direction of $a_2$, for example.

The holding part 24 is formed in an approximately semicircular flat plate, having a mounting recess 27 on which the sample 3 is placed and fixed. The holding part 24 is rotatably supported on the base part 22 in the directions of $b_1$, $b_2$ through a rotational shaft 28 rotatably at an angle of about ±30 degrees, for example. Moreover, to the mounting recess 27, the holding end side of the placed sample 3 is joined and fixed with a deposition film or solder material, for example.

The slide plate 25 is slidably disposed in the directions of arrows $c_1$, $c_2$ in FIG. 4 along the longitudinal direction of the base part 22. The tip end side of the slide plate 25 is slidably contacted with the arc-shaped outer part of the holding part 24, and the base end side thereof is drawn out of the vacuum container 10. Then, the slide plate 25 is manually operated in the directions of $c_1$, $c_2$, for example, and thus rotates the holding part 24 in the directions of $b_1$, $b_2$ in accordance with the sliding amount.

Figure 6:
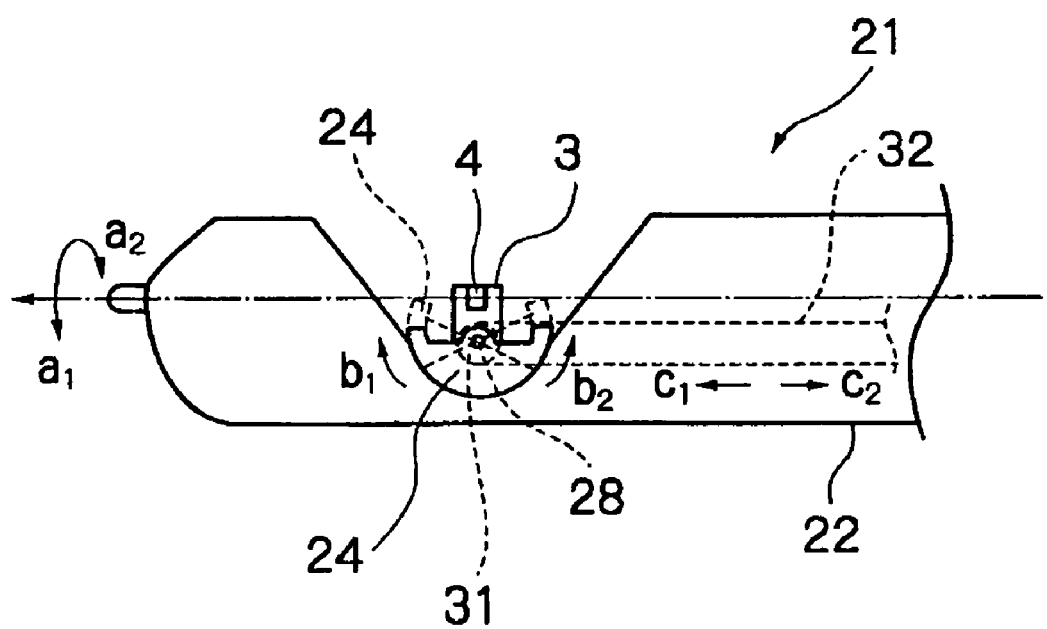
FIG. 6 is a perspective side view schematically illustrating an example of another drive mechanism which drives the holding part.

Furthermore, as shown in FIG. 6, for example, it is acceptable that the holding part 24 is configured to be rotated by a drive mechanism which has a pulley 31 and a belt 32 over the pulley 31. Moreover, not shown in the drawing, it is fine that the drive mechanism is configured of a wire, a gear and the like instead of the belt. Besides, it is acceptable that the holder member 21 is configured to have a so-called clamping mechanism in the holding part 24, the clamping mechanism clamps the sample 3 placed on the mounting recess 27.

The processing beam part 12 is a focused ion beam irradiation unit, for example, its lens-barrel is disposed vertically above the vacuum container 10, having a gallium liquid metal ion source which is a processing beam source (not shown in the drawing) and an ion optical system which focuses, scans and irradiates ion beams from the gallium liquid metal ion source. The processing beam part is disposed so that the irradiation axis (the center axis of the lens-barrel) of the focused ion beam is vertical with respect to the sample 3.

The removing beam unit or part 13 is a gaseous ion beam irradiation apparatus, for example, and is disposed at the position to approach the cross section 4 of the sample 3, having the removing beam source (gaseous ion gun) (not shown in the drawing) which irradiates an inert ion beam such as argon gas and helium gas of inert gas. The removing beam part 13 is disposed so that its irradiation axis (the center axis of the lens-barrel) toward the cross section 4 of the sample 3 is tilted at an angle of about 35 degrees in the upper slanting direction with respect to the horizontal direction. Furthermore, it is acceptable that the removing beam source is configured to irradiate an oxygen ion beam with oxygen as necessary. It is fine that a chemical species at this time is oxygen radicals other than oxygen ions.

Figure 7:
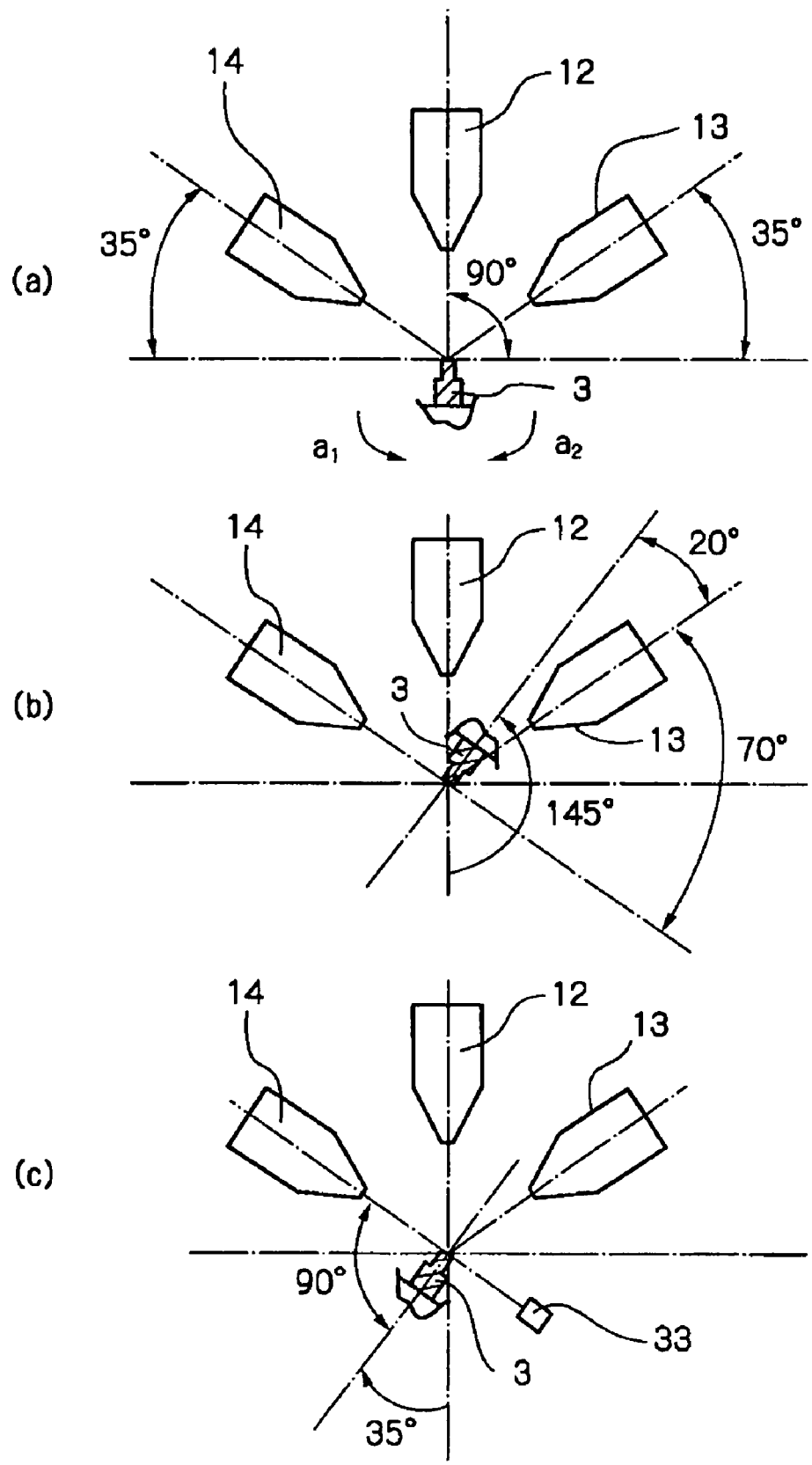
FIG. 7(a) is a schematic diagram illustrating a state that the cross section is processed in the sample.
FIG. 7(b) is a schematic diagram illustrating a state that an inert ion beam is irradiated onto the cross section of the sample.
FIG. 7(c) is a schematic diagram illustrating a state that an electron beam is irradiated onto the cross section of the sample.

The observing beam unit or part 14 is an electron beam irradiation apparatus, for example, and is disposed at the position to approach the cross section 4 of the sample 3, having an electron gun (not shown in the drawing) which irradiates an electron beam, and a TEM detector 33 which detects transmission electrons having been irradiated from the electron gun and transmitted through the cross section 4 of the sample 3. The observing beam part 14 is disposed so that its irradiation axis (the center axis of the lensbarrel) is tilted at an angle of about 35 degrees in the upper slanting direction with respect to the horizontal direction. As shown in FIGS. 1 and 7(c), the detector 33 is disposed at the position to face the electron gun as sandwiching the cross section 4 of the sample 3. In addition, the observing beam part 14 described above takes the transmission mode, but is acceptable to configure to have the reflection mode in which the detector is disposed at the position to approach the top surface side of sample 3, for example, and detects secondary electrons reflected in the cross section 4.

A method in which the ion beam apparatus 1 thus configured is used to process the observation cross section 4 in the sample 3 and to observe the cross section 4 will be describe with reference to the drawings.

First, when the ion beam apparatus 1 processes the cross section 4 in the sample 3 as shown in FIG. 7(a), the irradiating direction of the focused ion beam is approximately orthogonal to the top surface of the sample 3 at the initial position where the sample is held by the holding part 24 of the holder member 21. At the initial position, a processing beam source irradiates the focused ion beam onto the sample 3 to form the cross section 4.

Here, problems traditionally generated in irradiating the focused ion beam onto the sample to process the cross section will be described briefly.

Figure 12:
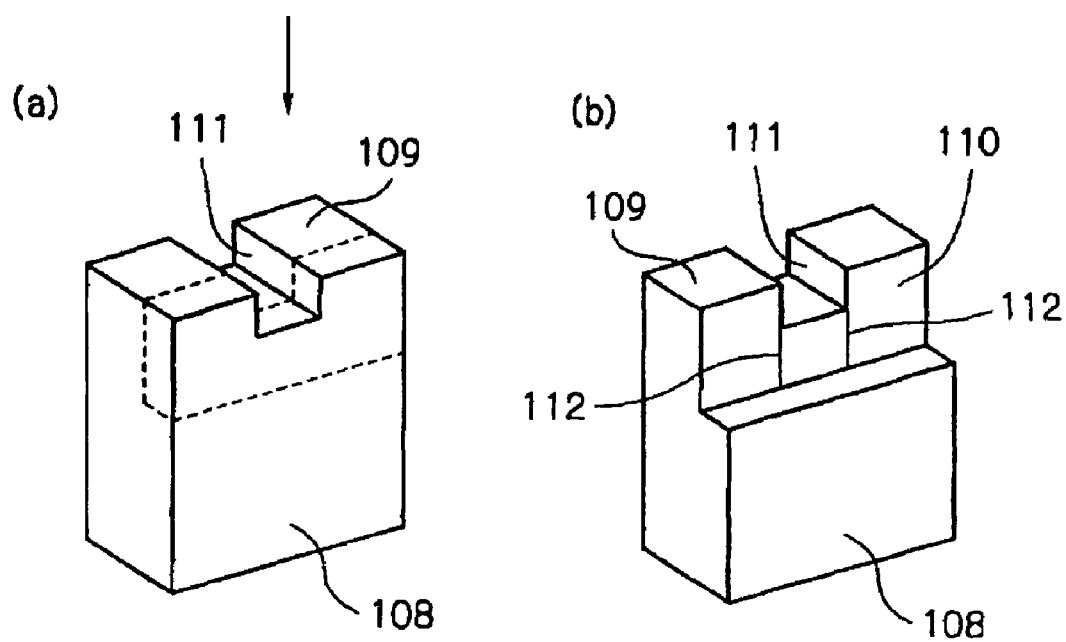
FIG. 12(a) is a schematic diagram illustrating a sample in which a cross section is formed by a focused ion beam in a conventional method.
FIG. 12(b) is a schematic diagram illustrating the sample in which streaks are formed on the cross section by the focused ion beam in the conventional method.

As schematically shown in FIG. 12(a), when a recess 111 is on a top surface (front surface) 109 of a sample 108 to approach the processing beam source side, variations occur in the processing rate depending on the shape of the top surface 109 of the sample 108. Therefore, as shown in FIG. 12(b), a problem arises that streaks 112 in bumps and dips are generated on a cross-section 110 along their radiating direction of the focused ion beam on the borders of the recess 111. Furthermore, these streaks 112 are also generated when the border between different materials exist on the top surface 109 of the sample 108. Similarly, a problem also arises that an argon ion beam is irradiated onto the cross section 110 of the sample 108 to generate streaks when a fracture layer is removed from the cross section 110.

Then, these streaks 112 are generated on the cross section 110 of the sample 108 to cause harm to obtaining an excellent observed image of the cross section 110 in observation by the observing beam part.

Figure 8:
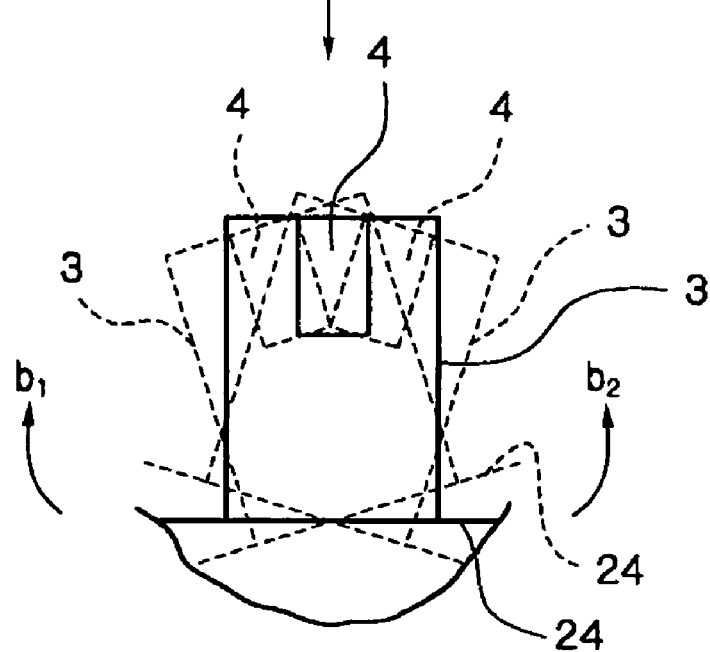
FIG. 8 is a schematic diagram illustrating a sample in which a cross section is formed by a focused ion beam while the cross section is rotated to different positions with respect to the irradiating direction of the focused ion beam.

For measures against these problems, in the embodiment, as shown in FIG. 8, when the cross section 4 is processed in the sample 3 by the focused ion beam, the holding part 24 is rotated in the directions of $b_1$, $b_2$. Thus, the cross section 4 is rotated at the position where it is tilted only at a desired angle with respect to the irradiating direction of the focused ion beam, and then processing by the focused ion beam is repeated at least more than once. Accordingly, streaks generated by fine bumps and dips and the border between different materials on the top surface of the sample 3 are removed from the cross section 4 of the sample 3 and gradually reduced as processing is repeated, and then a smooth cross section 4 with inconspicuous streaks is formed.

Subsequently, as shown in FIG. 7(b), the ion beam apparatus 1 rotates the holder member 21 at an angle of about 145 degrees, for example, in the direction of $a_1$ from the initial position, and adjusts the irradiating direction of an inert ion beam by the removing beam part 13, the beam is irradiated onto the cross section 4 of the sample 3 held by the holding part 24.

Figure 9:
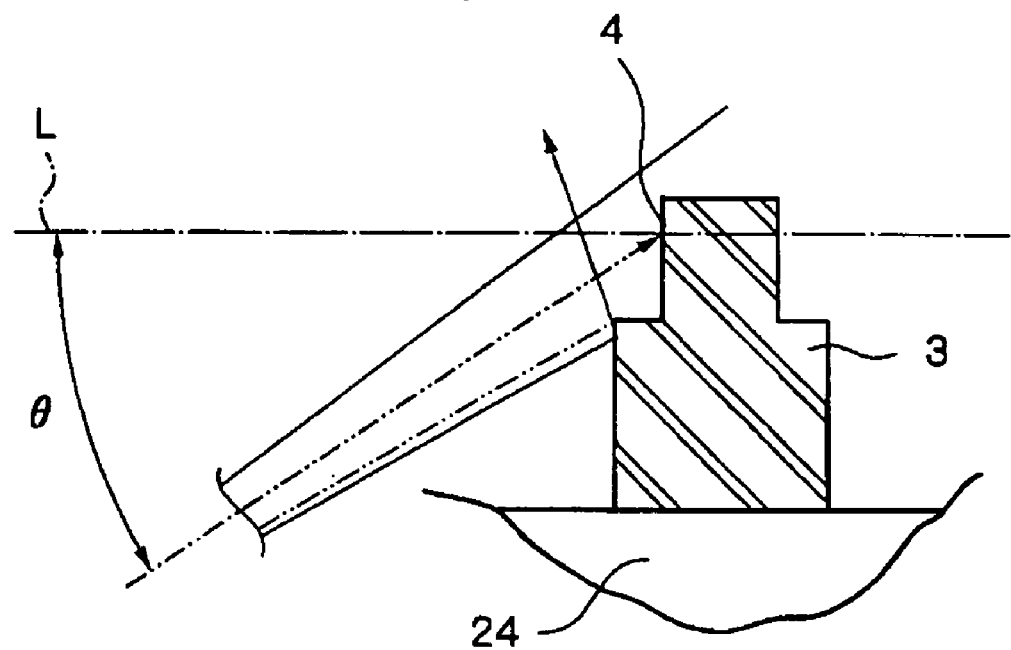
FIG. 9 is a schematic diagram illustrating a processing state that a cross section is rotated in the irradiating direction of an inert ion beam that is irradiated onto a cross section of a sample.

More specifically, as shown in FIG. 9, to the sample 3 held by the holder member 21, the removing beam source is positioned on the holding end side of the sample 3 with respect to the normal L perpendicular to the cross section 4 when the inert ion beam is irradiated onto the cross section 4, and the irradiating direction of the inert ion beam to be irradiated onto the cross section 4 is tilted at the tilt angle θ with respect to the normal L. The tilt angle θ ranges in 90°>θ>0°, and a large angle θ is fine as much as possible depending on the shape of the sample 3 and the size and the like of the holding part 24. In the embodiment, it is set from about 70 to 80 degrees, for example.

Then, for the sample 3, the irradiating direction of the inert ion beam for the cross section 4 is tilted at the tilt angle 8 with respect to the normal L. Thus, the inert ion beam is irradiated onto the side surface of the step part adjacent to the cross section 4 and secondary particles of the fracture layer are ejected or flown. However, the flown secondary particles travel in the direction where they do not reach the cross section 4. Therefore, it is reduced that the secondary particles removed from the fracture layer of the cross section 4 are again attached onto the cross section 4 to contaminate the cross section 4.

Similarly, as shown in FIG. 8, when the fracture layer is removed from the cross section 4 of the sample 3 by the inert ion beam, the holding part 24 is also rotated in the directions of $b_1$, $b_2$. Thus, the cross section 4 is rotated at the position where it is tilted only at a desired angle with respect to the irradiating direction of the inert ion beam, and processing by the inert ion beam is repeated at least more than once. Accordingly, streaks generated by fine bumps and dips and the border between different materials on the top surface of the sample 3 are removed from the cross section 4 of the sample 3 and gradually reduced as processing is repeated, and then a smooth cross section 4 with inconspicuous streaks is formed.

Furthermore, to the sample 3, the inert ion beam is irradiated onto the other cross section 4 at the position at an angle of about 40 degrees rotated in the direction of $a_2$ from the position where the inert ion beam has been irradiated onto one of the cross sections 4, and then the fracture layer is removed.

Moreover, it is acceptable that when the cross section 4 is processed by the focused ion beam and the fracture layer is removed by the inert ion beam in order to remove above-described streaks generated on the cross section 4 of the sample 3, the focused ion beam or inert ion beam is irradiated onto the sample 3 while the holding part 24 is being rotated in the directions of $b_1$, $b_2$, and thus processing is done as the irradiating direction of the focused ion beam or inert ion beam is varied to the sample 3.

In this embodiment, the holding part 24 is rotated when the cross section 4 is processed by the focused ion beam and the fracture layer is removed by the inert ion beam in order to remove streaks. However, it is acceptable that streaks are collectively removed when the fracture layer is removed by the inert ion beam. In addition, when streaks are collectively removed by the inert ion beam, the irradiating direction of the inert ion beam with respect to the cross section 4 needs to be varied from the irradiating direction of the focused ion beam with respect to the sample 3.

Lastly, as shown in FIG. 7(c), the ion beam apparatus 1 rotates the holder member 21 at an angle of 180 degrees in the direction of $a_2$, for example, from the rotational position where the inert ion beam has been irradiated, that is, the apparatus rotates it at an angle of 35 degrees in the direction of $a_2$ with respect to the initial position. Therefore, the irradiating direction of the electron beam by the observing beam part 14 is adjusted, the beam is irradiated onto the cross section 4 of the sample 3 held by the holding part 24. At the rotational position, the observing beam part 14 irradiates the electron beam onto the cross section 4 of the sample 3, the detector 33 detects transmission electrons having been transmitted through the cross section 4, and thus an excellent observed image of the cross section 4 can be obtained.

As described above, the ion beam apparatus 1 rotates the holder member 21 in the directions of $a_1$, $a_2$, it tilts the irradiating direction of the inert ion beam with respect to the cross section 4 of the sample 3 only at the tilt angle θ to the normal L of the cross section 4, and then the fracture layer is removed. Thus, it can be reduced that the secondary particles of the removed fracture layer are again attached onto the cross section. On this account, according to the ion beam apparatus 1, the smooth cross section 4 with the fracture layer excellently removed can be obtained, and the cross section 4 can be observed by the observing beam part 14 excellently.

Furthermore, the holder part 11 provided to the ion beam apparatus 1 has the holder member 21 having the holding part 24 rotatably disposed in the directions of $b_1$, $b_2$, and thus streaks generated in the cross section 4 of the sample 3 that is processed by the focused ion beam can be small to improve smoothness of the cross section 4.

Lastly, in the ion beam apparatus 1 described above, the removing beam part 13 is disposed in the upper slanting direction with respect to the sample 3 on the holder member 21. Another ion beam apparatus 2 in which the removing beam part 13 is disposed at a different position will be described briefly with reference to FIG. 10. In addition, as compared with the ion beam apparatus 1 described above, since the ion beam apparatus 2 is varied at the positions of the removing beam part 13 and the observing beam part 14, the same reference numerals and signs are used to designate the same components and a description thereof is omitted.

Figure 10:
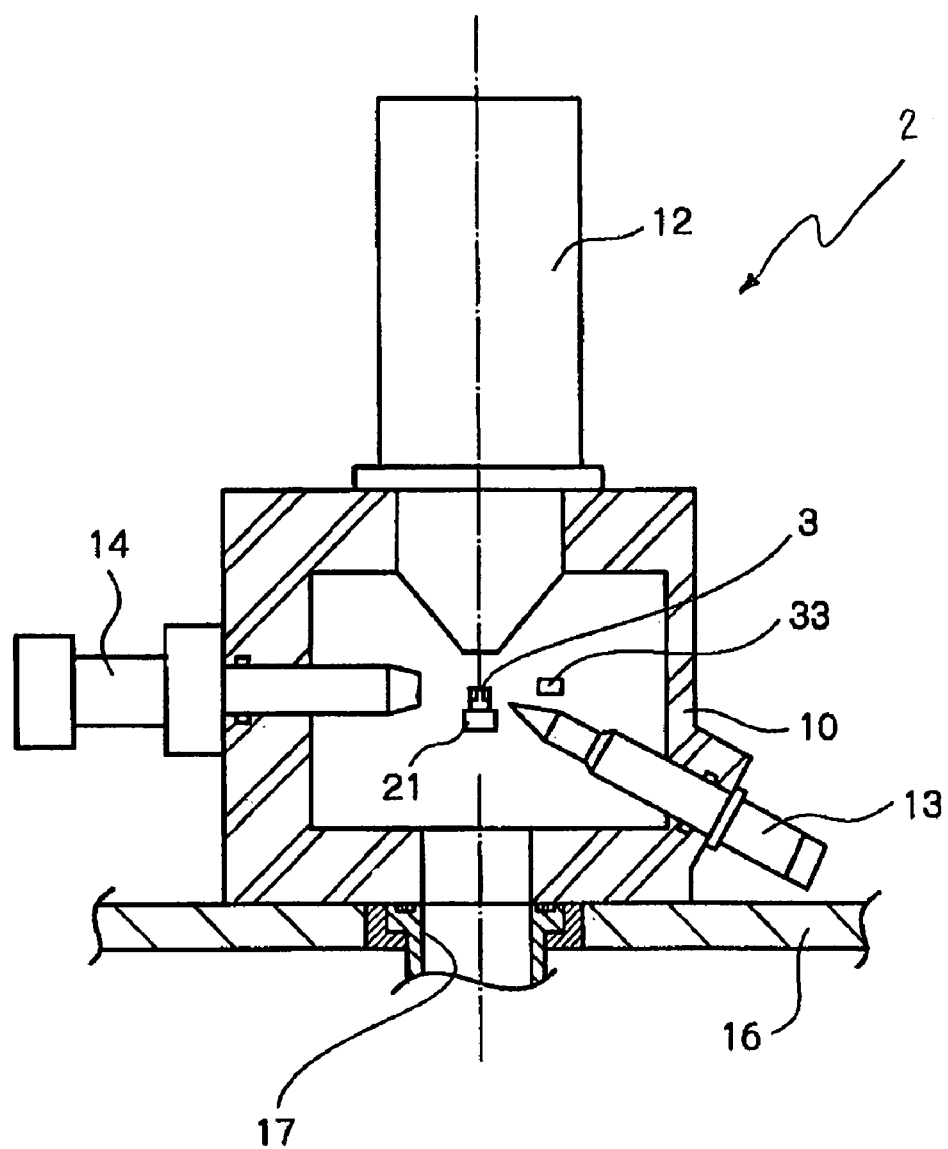
FIG. 10 is a cross section schematically illustrating an example of another ion beam apparatus according to the invention.
Figure 11:
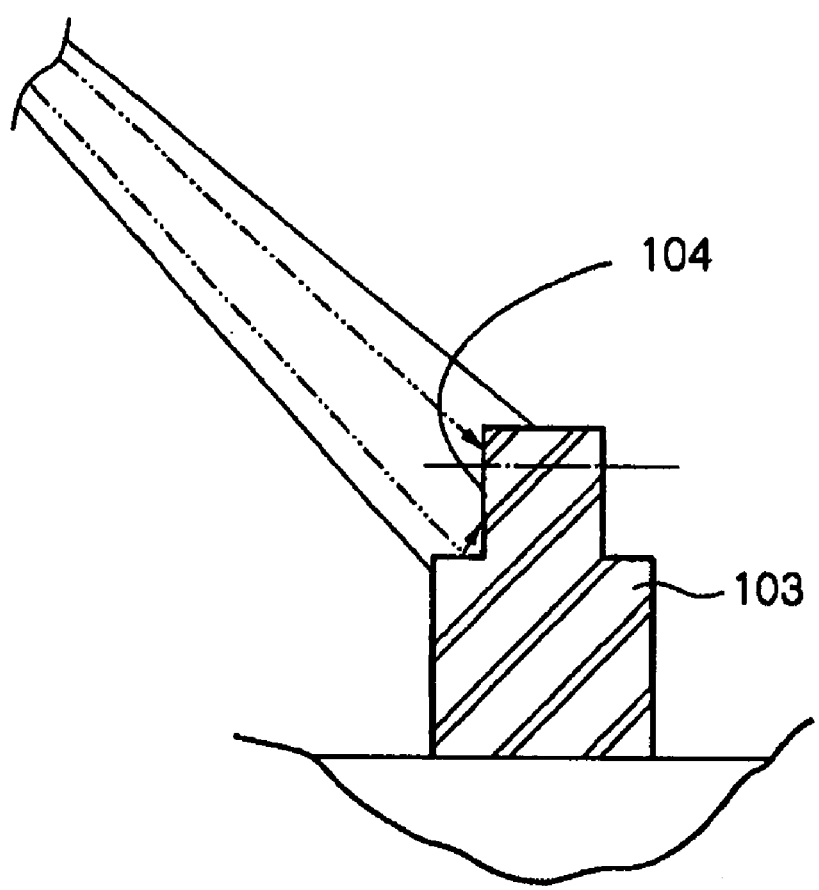
FIG. 11 is a schematic diagram for describing a state that an the inert ion beam is irradiated onto a cross section of a sample.

As shown in FIG. 10, in the ion beam apparatus 2, a removing beam part 13 is disposed so as to irradiate an inert ion beam onto a sample 3 on a holder member 21 from the lower slanting direction, and an observing beam part 14 is disposed so as to irradiate an electron beam onto the sample 3 on the holder member 21 from the horizontal direction.

According to the ion beam apparatus 2 thus configured, the holder member 21 does not need to be rotated in the directions of $a_1$, $a_2$, and therefore the configuration of the holder member 21 can be simplified. Furthermore, it is acceptable that in the ion beam apparatus, the relative position of the removing beam part 14 with respect to a cross section 4 of the sample 3 can be set depending on the rotational range of the holder member 21 in the directions of $a_1$, $a_2$.

Therefore, it is acceptable that the ion beam apparatus according to the invention is configured in which the holder part 11, the removing beam part 13 and the observing beam part 14 are disposed at given positions when it is configured in which the inert ion beam is irradiated from the holding end side of the sample 3 with respect to the normal L of the cross section 4 of the sample 3 so that its irradiating direction is tilted with respect to the normal L.

In addition, the embodiment is configured as the side entry ion beam apparatus 1 having the processing beam part 12, but it is not limited to this configuration. For example, it can be configured to have the holder part 11 and the removing beam part 13 without the processing beam part 12, and to have the observing beam part 14 in addition to this configuration.

INDUSTRIAL APPLICABILITY

As described above, according to the ion beam apparatus of the invention, it is provided with the removing beam source which irradiates the gaseous ion beam from the holding end side of the sample with respect to the direction vertical to the processed surface of the sample so that its irradiating direction is tilted with respect to the vertical direction. Thus, it is reduced that the fracture layer removed by the gaseous ion beam is again attached onto the processed surface. Accordingly, the ion beam apparatus according to the invention can excellently remove the fracture layer from the processed surface, and a smooth processed surface can be obtained.

Furthermore, in the ion beam apparatus according to the invention, the holder member has the base part which is rotatably supported about the first axis in parallel with the horizontal direction, and the holding part which is rotatably disposed about the second axis orthogonal to the first axis at the tip end side of the base part and holds the sample. Thus, the arrangement of the removing beam source with respect to the holder member and the flexibility in the irradiating direction of the gaseous ion beam are secured, and the irradiating direction of the ion beam can be varied with respect to the processed surface of the sample held by the holding part.

Moreover, according to the ion beam processing method of the invention, the gaseous ion beam is irradiated from the holding end side of the sample with respect to the direction vertical to the processed surface of the sample at the second step so that its irradiating direction is tilted with respect to the vertical direction. Thus, it can be reduced that the fracture layer removed by the gaseous ion beam is again attached onto the processed surface, and the fracture layer can be excellently removed from the processed surface to obtain a smooth processed surface.

Besides, according to the holder member of the invention, it has the base part which is rotatably supported about the first axis in parallel with the horizontal direction, and the holding part which is rotatably disposed about the second axis orthogonal to the first axis at the tip end side of the base part and holds the sample where the focused ion beam is irradiated to form the processed surface. Therefore, the irradiating directions of the focused ion beam and the gaseous ion beam can be varied with respect to the processed surface of the sample. Accordingly, according to the holder member of the invention, the irradiating direction of the focused ion beam or the gaseous ion beam can be varied for processing to reduce streaks to be generated in the processed surface. Thus, smoothness of the processed surface can be improved.

The invention claimed is:

1. An ion beam apparatus comprising:
   a holder member that holds a sample by holding an end of the sample;
   a focused ion beam unit that forms a cross section in a portion of the sample by irradiating a focused ion beam onto the sample from above and approximately orthogonally to top surface of the sample held by the holder member; and
   a removing beam unit that irradiates a gaseous ion beam onto the cross section of the sample held by the holder member and removes a fracture layer from the cross section, the gaseous ion beam being irradiated from the held end side of the sample so that its irradiating direction is tilted with respect to a normal to the cross section.

2. An ion beam apparatus according to claim 1; wherein the gaseous ion beam is an inert gas ion beam.

3. An ion beam apparatus according to claim 1; wherein the holder member comprises a base part which is rotatably supported about a first axis parallel with the horizontal direction, and a holding part which is rotatably disposed about a second axis, orthogonal to the first axis, at a tip end side of the base part and holds the sample where the focused ion beam is irradiated to form the cross section.

4. An ion beam apparatus according to claim 3; further including a drive mechanism that rotates the holding part about the second axis.

5. An ion beam apparatus according to claim 1; further comprising an observation beam unit that irradiates an electron beam onto the cross section of the sample to enable observation of the cross section.

6. An ion beam apparatus comprising:
   a holder member that holds a sample by holding an end of the sample;
   a focused ion beam unit that forms a cross section in a portion of the sample by irradiating a focused ion beam onto the sample from vertically above the sample held by the holder member; and
   a removing beam unit that irradiates a gaseous ion beam onto the cross section of the sample held by the holder member and removes a fracture layer from the cross section, the removing beam unit being disposed so that the gaseous ion beam is irradiated from a lower slanting direction with respect to the held sample by the holder member.

7. An ion beam apparatus according to claim 6; further including an observing beam unit disposed so as to irradiate an electron beam onto the sample held by the holder member from the horizontal direction.

8. An ion beam apparatus according to claim 7; further comprising an observation beam unit that irradiates an electron beam onto the cross section of the sample to enable observation of the cross section.

9. An ion beam processing method comprising:
- a first step of holding a sample to be processed by holding the sample at an end thereof;
- a second step of irradiating a focused ion beam onto the held sample from above to form a cross section in a portion of the sample; and
- a third step of irradiating a gaseous ion beam onto the cross section of the sample and removing a fracture layer from the cross section, the gaseous ion beam being irradiated from the held end side of the sample so that its irradiating direction is tilted with respect to a normal to the cross section of the sample.

10. An ion beam processing method according to claim 9; wherein the gaseous ion beam is an inert gas ion beam.

11. An ion beam processing method according to claim 10; wherein in the third step, the irradiating direction of the inert gas ion beam is varied with respect to the sample.

12. An ion beam processing method according to claim 11; wherein in the second step or the third step, the sample is moved with respect to the irradiating direction of the focused ion beam or the inert gas ion beam through a holder which holds the sample.

13. An ion beam processing method according to claim 9; wherein in the third step, the irradiating direction of the gaseous ion beam is varied with respect to the sample.

14. An ion beam processing method according to claim 13; wherein in the second step, the irradiating direction of the focused ion beam is varied with respect to the sample.

15. An ion beam processing method according to claim 14; wherein in the second step or the third step, the sample is moved with respect to the irradiating direction of the focused ion beam or the gaseous ion beam through a holder which holds the sample.

* * * * *